(12) United States Patent
Kitagawa et al.

(10) Patent No.: US 9,181,436 B2
(45) Date of Patent: Nov. 10, 2015

(54) COSMETIC PIGMENTS, THEIR PRODUCTION METHOD, AND COSMETICS CONTAINING THE COSMETIC PIGMENTS

(75) Inventors: Masaru Kitagawa, Osaka (JP); Kenji Nishimoto, Osaka (JP); Takumi Tanaka, Osaka (JP)

(73) Assignees: TOYOBO CO., LTD., Osaka-shi (JP); DAITO KASEI KOGYO CO., LTD., Osaka-shi (JP)

( * ) Notice: Subject to any disclaimer, the term of this patent is extended or adjusted under 35 U.S.C. 154(b) by 0 days.

(21) Appl. No.: 13/498,200

(22) PCT Filed: Sep. 27, 2010

(86) PCT No.: PCT/JP2010/066661
§ 371 (c)(1),
(2), (4) Date: Mar. 26, 2012

(87) PCT Pub. No.: WO2011/040357
PCT Pub. Date: Apr. 7, 2011

(65) Prior Publication Data
US 2012/0183592 A1 Jul. 19, 2012

(30) Foreign Application Priority Data
Sep. 29, 2009 (JP) .................. 2009-223600

(51) Int. Cl.
*A61K 8/02* (2006.01)
*C09C 3/10* (2006.01)
*A61K 8/60* (2006.01)
*A61Q 1/02* (2006.01)
*A61Q 1/06* (2006.01)
*A61Q 17/04* (2006.01)

(52) U.S. Cl.
CPC ............... *C09C 3/10* (2013.01); *A61K 8/0241* (2013.01); *A61K 8/602* (2013.01); *A61Q 1/02* (2013.01); *A61Q 1/06* (2013.01); *A61Q 17/04* (2013.01); *A61K 2800/612* (2013.01)

(58) Field of Classification Search
CPC ....... A61K 8/0241; A61K 8/602; A61Q 1/02; A61Q 1/06; A61Q 17/04
See application file for complete search history.

(56) References Cited

U.S. PATENT DOCUMENTS

| | | | |
|---|---|---|---|
| 6,080,424 A * | 6/2000 | Avalle .......................... | 424/450 |
| 7,820,150 B2 * | 10/2010 | Kohlhase et al. .......... | 424/70.28 |
| 2004/0228888 A1 | 11/2004 | Kohlhase et al. | |
| 2010/0004472 A1 | 1/2010 | Kitagawa et al. | |
| 2011/0257116 A1 | 10/2011 | Kitagawa et al. | |

FOREIGN PATENT DOCUMENTS

| | | |
|---|---|---|
| CN | 1282766 A | 2/2001 |
| CN | 1352670 A | 6/2002 |
| EP | 1 440 684 A1 | 7/2004 |
| EP | 1 964 546 A1 | 9/2008 |
| JP | 61-69710 A | 4/1986 |
| JP | 8-291020 A | 11/1996 |
| JP | 2000-256131 A | 9/2000 |
| JP | 2001-2524 A | 1/2001 |
| JP | 2007-119741 A | 5/2007 |
| JP | 2009-167158 A | 7/2009 |
| JP | 2009-167159 A | 7/2009 |
| JP | 2009-201478 A | 9/2009 |
| JP | 2009201478 A * | 9/2009 ............ C12P 19/44 |

OTHER PUBLICATIONS

International Search Report of PCT/JP2010/066661, mailing date of Oct. 26, 2010.
Chinese Office Action dayed Jan. 14, 2013, issued in corresponding Chinese Patent Application No. 201080042817.5, with English translation (10 pages).
Notification of Transmittal of Translation of the International Preliminary Report on Patentability (Form PCT/IB/338) of International Application No. PCT/JP2010/066661 mailed May 18, 2012 with Forms PCT/IB/373 and PCT/ISA/237.
Kitamoto et al., "Functions and Potential Applications of Glycolipid Biosurfactants from Energy-Saving Materials to Gene Delivery Carries", Journal of Bioscience and Bioengineering, vol. 94, No. 3, pp. 187-201, Jan. 1, 2002 (in English) (16 pages).
Holmberg, "Natural Surfactants", Current Opinion in Colloid & Interface Science, vol. 6, No. 2, pp. 148-159, May 1, 2001 (in English) (12 pages).
Kitamoto et al., "Self-assembling properties of glycolipid biosurfactants and their potential applications", Current Opinion in Colloid & Interface Science, London, GB, vol. 14, No. 5, pp. 315-328, May 23, 2009 (in English) (14 pages).
Extended European Search Report dated Aug. 7, 2015, issued in corresponding Application No. 10820472.8. (in English) (8 pages).

* cited by examiner

*Primary Examiner* — Lezah Roberts
*Assistant Examiner* — Nannette Holloman
(74) *Attorney, Agent, or Firm* — Westerman, Hattori, Daniels & Adrian, LLP

(57) ABSTRACT

To provide cosmetic pigments that are human-body friendly with good skin adhesion and that provide good feeling, their production method, and cosmetics containing such cosmetic pigments which provide fresh and enriched feeling accordingly.
Pigment surfaces are coated with mannosylerythritol lipid, which is glucolipids, consisting of mannose, sugar alcohol and a fatty acid as shown in the general expression (1) below:

[Formula 11]

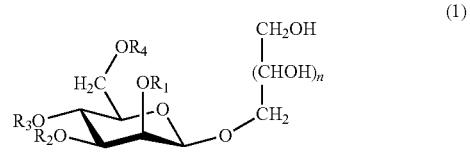

(1)

(Note: In the general expression, $R_1$ and $R_2$ denote aliphatic acyl group with carbon numbers 6 through 20, which can be either same or different. $R_3$ and $R_4$ denote hydrogen or acetyl group, which can be either same or different. n denotes an integer in the range of 2 to 4.)

8 Claims, No Drawings

COSMETIC PIGMENTS, THEIR PRODUCTION METHOD, AND COSMETICS CONTAINING THE COSMETIC PIGMENTS

TECHNICAL FIELD

The present invention relates to cosmetic pigments, their production method, and cosmetics containing the cosmetic pigments, which cosmetic pigments are suitable to be contained in makeup products such as foundations, eyeshadow and lipsticks or basic skin care such as sunscreen products, emulsions and creams.

BACKGROUND ART

Conventionally, pigments whose surfaces are coated with various types of compounds have been used as pigments to be contained in makeup products such as foundations, eyeshadow and blushers or basic skin care such as sunscreen products, emulsions and creams with a view to improve waterproofness and avoid coming off of makeup or to improve feeling of the pigments and so forth.

Here, coating pigment surfaces with a silicone compound or a fluorine compound has been known as a means of improving the waterproofness (see Patent Documents 1 and 2). Cosmetic pigments whose surfaces are coated with the silicone compound or fluorine compound excel in avoiding coming off of makeup and contribute to long-lasting makeup because waterproofness is imparted to them. However, there are some problems that they give a dried out and less moist feeling owing to the compounds, and skin adhesion becomes poor because they have less affinity to a biological body.

Meanwhile, coating pigment surfaces with collagen has been known as a means of improving feeling of the pigments (see Patent Document 3). However, since the collagen is an animal protein, there is a limit in the use of it, which is a problem.

Recently, due to the increasing popularity of natural products among consumers, cosmetics using compounds derived from natural products are greatly desired, and development of cosmetics which are human-body friendly having good skin adhesion and which provide good feeling are strongly desired.

Surfactants (biosurfactants) such as glucolipids are said to have great biodegradability and low toxicity and they are environmentally-friendly. Therefore, applying them to a food industry, cosmetic industry, drug industry, chemical industry, environmental field etc. has been considered. However, existing biosurfactants have poor hydrophobicity, so that they are not suitable for cosmetic pigments. Meanwhile, although mannosylerythritol lipid (MEL) has been known, for use in skin care, as having curative properties against skin roughness because it can easily form a lamellar structure, there has been no report that it is used as cosmetic pigments.

PRIOR LITERATURES

[Patent Document 1] Japanese Patent Laid-Open Publication No. 2007-119741
[Patent Document 2] Japanese Patent Laid-Open Publication No. 2001-2524
[Patent Document 3] Japanese Unexamined Patent Application Publication No. Sho 61-69710

SUMMARY OF THE INVENTION

Problems to be Solved by the Invention

The present invention is made in view of the above problems and an object of the present invention is to provide cosmetic pigments that are human-body friendly with good skin adhesion and that provide good feeling, their production method, and cosmetics containing such cosmetic pigments which provide fresh and enriched feeling accordingly.

Means of Solving the Problems

In order to achieve the above object, the present invention tries to obtain novel functional pigments and cosmetics by coating pigment surfaces with mannosylerythritol lipid, i.e., glucolipids produced by yeasts etc., that is derived from olive oil and the like.

In summary, the first invention is directed to cosmetic pigments whose surfaces are coated with mannosylerythritol lipid, which is glucolipids, consisting of mannose, sugar alcohol and a fatty acid as shown in the general expression (1) below:

[Formula 1]

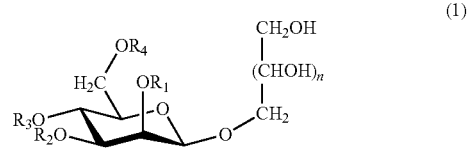

(1)

(Note: In the general expression, $R_1$ and $R_2$ denote aliphatic acyl group with carbon numbers 6 through 20, which can be either same or different. $R_3$ and $R_4$ denote hydrogen or acetyl group, which can be either same or different. n denotes an integer in the range of 2 to 4.)

The second invention is directed to a method of producing the cosmetic pigments characterized in that the pigment surfaces are coated with mannosylerythritol lipid shown in the above general expression (1) by dissolving or dispersing mannosylerythritol lipid in an organic solvent, agitatedly mixing the compound liquid with the pigments, then removing the organic solvent.

The third invention is directed to cosmetics containing the cosmetic pigments according to the first invention. In the fourth invention, cosmetics according to the third invention are either one of powder foundations, water-in-oil foundations, water-in-oil sunscreens or lip primers.

Effect of the Invention

Since mannosylerythritol lipid according to the first and second inventions is derived from natural products such as olive oil and soy oil, it is safe to a human body. In addition, since mannosylerythritol lipid for coating the surfaces of the pigments is an amphipathic compound having both hydrophobicity deriving from lipid property and hydrophilicity deriving from a property of sugar, it has a structure similar to a ceramide that constitutes the sebum membrane of a human. Although conventional biosurfactants are not suitable for cosmetic pigments as they have poor hydrophobicity, mannosylerythritol lipid according to the present invention can provide pigments with water-resistant property so that the conventional problem can be solved. Cosmetic pigments with good skin adhesion which also provide fresh and enriched feeling and excel in stability of such effects can be thus obtained.

Also, since the cosmetics according to the third and fourth inventions contain the cosmetic pigments according to the first invention, they have excellent skin adhesion and skin affinity and ensure the high-safeness. In addition, thanks to the hydrophobicity effect deriving from the lipid property, it becomes possible to provide the pigments with the water-resistant property, which contributes to long-lasting makeup. Furthermore, because of a moisturizing effect of the hydrophilicity deriving from the property of sugar, cosmetics with fresh and enriched feeling can be obtained.

DETAILED DESCRIPTION OF PREFERRED EMBODIMENTS

Next, concrete description of preferred embodiments of the cosmetic pigments, their production method and cosmetics containing the cosmetic pigments according to the present invention will be made.

Mannosylerythritol lipid (often referred to hereinafter as "MEL") in the present invention is glucolipids consisting of mannose, sugar alcohol and a fatty acid as shown in the general expression (1) below:

[Formula 2]

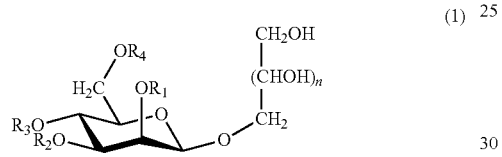

(1)

(Note: In the general expression, $R_1$ and $R_2$ denote aliphatic acyl group with carbon numbers 6 through 20, which can be either same or different. $R_3$ and $R_4$ denote hydrogen or acetyl group, which can be either same or different. n denotes an integer in the range of 2 to 4.)

MEL is a material found from *Ustilago nuda* and *Shizonella melanogramma*. Later, it is known that MEL can be produced by yeasts such as *Candida* yeast that is an itaconic acid producing mutated strain, *Candida antarctia* (currently called as *Pseudozyma antarctica*), and *Kurtzmanomyces* yeast.

There are various kinds of MELs according to presence or absence of the acetyl group added to the mannose residues $R_3$, $R_4$ in the above general expression (1); kinds of sugar alcohol that are glycosidically-bound to the mannose; or isomeric forms of the sugar alcohol.

Mannosylerythritol lipids that are suitable for the present invention are as follows: MEL-A having a structure shown in the below general expression (2); MEL-B having a structure shown in the below general expressions (3) or (4); MEL-C having a structure shown in the below general expression (5) and MEL-D having a structure shown in the below general expressions (6) or (7). Among them, the MEL-A produced by *Pseudozyma antarctica* having the structure shown in the general expression (2) and the MEL-B produced by *Pseudozyma tsukubaensis* having the structure shown in the general expression (4) are particularly suitable.

The general expressions (2), (3), (5) and (6) below have 4-O-β-O-mannopyranosyl-(2S,3R)-erythritol structure. Meanwhile, a term "inverted" is used for distinguishing MELs in which an optical isomer exists. In the present invention, compounds having 4-O-β-D-mannopyranosyl-meso-(2R,3S)-erythritol structure are inverted as shown in the below general expressions (4) and (7).

[Formula 3]

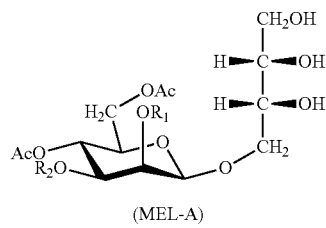

(2)

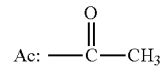

[Formula 4]

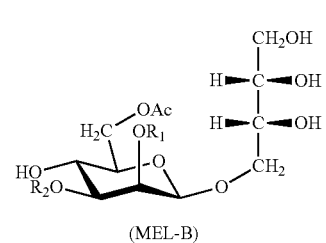

(3)

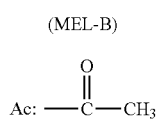

[Formula 5]

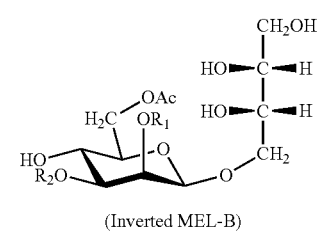

(4)

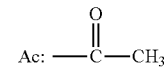

[Formula 6]

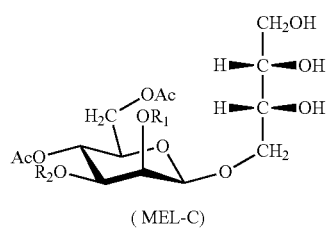

(5)

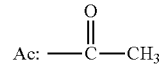

[Formula 7]

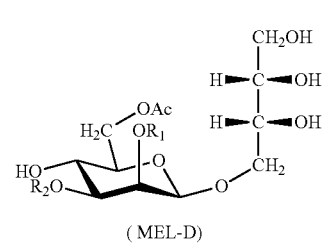

(6)

-continued

[Formula 8]

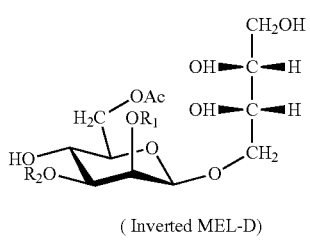

(Inverted MEL-D)

(Substituent groups $R_1$ and $R_2$ in the general expressions (2), (3), (4), (5), (6) and (7) denote aliphatic acyl group with carbon numbers 6 through 20, which can be either same or different.)

Although one of the aforementioned MEL-A to MEL-D may be used as a mannosylerythritol lipid, two types or more of mannosylerythritol lipids may be used in combination.

As pigments to be coated with the glucolipids that is shown in the above general expression (1), various, existing known pigments may be used regardless of their forms (spherical, bar-like, needle-like, plate-like, infinite, scale-like, spindle-shaped etc.), particle sizes (haze particles, fine particles, as small as pigment class etc.), or particle structures (porous, imperforate etc.). Examples of such pigments include inorganic powders, organic powders, surfactant metal salt powders, colored pigments, pearl pigments and metal powder pigments.

More specifically, inorganic powders include: titanium oxide; zirconium oxide; zinc oxide; cerium oxide; magnesium oxide; barium sulfate; calcium sulfate; magnesium sulfate; calcium carbonate; magnesium carbonate; talc; mica; kaolin; sericite; white mica; synthetic mica; bronze mica; lepidolite; iron mica; lithia mica; silicic acid; silicic anhydride; aluminum silicate; magnesium silicate; magnesium aluminum silicate; calcium silicate; barium silicate; strontium silicate; tungstic acid metal salt; hydroxyapatite; vermiculite; higilite; bentonite; montmorillonite; hectorite; zeolite; ceramics powder; dicalcium phosphate; alumina; aluminum hydroxide; boron nitride; silica and so on.

Organic powders include: polyamide powder; polyester powder; polyethylene powder; polypropylene powder; polystyrene powder; polyurethane powder; benzoguanamine powder; polymethyl benzoguanamine powder; polytetrafluoroethylene powder; polymethylmethacrylate powder; cellulose; silk powder; nylon powder; nylon 12; nylon 6; acrylic powder; acrylic elastomer; styrene-acrylic acid copolymer; divinylbenzen-styrene copolymer; vinyl resin; urea resin; phenol resin; fluorine resin; silicon resin; acrylic resin; melamine resin; epoxy resin; polycarbonate resin; microcrystal fiber powder; starch powder; lauroyl lysine and so on.

Surfactant metal salt powder (metallic soap) include: zinc stearate; aluminum stearate; calcium stearate; magnesium stearate; zinc myristate; magnesium myristate; zinc cetyl phosphate; calcium cetyl phosphate; sodium zinc cetyl phosphate and so on.

Colored pigments include: inorganic red pigments such as iron oxide, ferric hydroxide and iron titanate; inorganic brown pigments such as γ-iron oxide; inorganic yellow pigments such as yellow iron oxide and yellow ocher; inorganic black pigments such as black iron oxide and carbon black; inorganic purple pigments such as manganese violet and cobalt violet; inorganic green pigments such as chromium hydroxide, chrome oxide, cobalt oxide and cobalt titanate; inorganic blue pigments such as iron blue and ultramarine; particulate powders such as particulate titanium oxide, particulate cerium oxide and particulate zinc oxide; laked tar dyes; laked natural dyes; and synthetic resin powders combining foregoing powders.

Pearl pigments include titanium oxide coated mica; bismuth oxychloride; titanium oxide coated bismuth oxychloride; titanium oxide coated talc; argentine and titanium oxide-coated colored mica.

Metal powder pigments include powders selected from aluminum powder, copper powder, stainless powder and so on.

In a treatment method for obtaining cosmetic pigments of the present invention, mannosylerythritol lipid as shown in the above general expression (1) is dissolved or dispersed in a proper organic solvent. This compound liquid is stirred and mixed with intended pigments, then the organic solvent is removed so that cosmetic pigments whose surfaces are treated with coating are obtained.

Organic solvent used in this treatment method includes alcohol such as ethanol, isopropyl alcohol and isobutyl alcohol; hydrocarbon system organic solvent such as toluene, n-hexane and cyclohexane; polar organic solvent such as acetone, ethyl acetate and butyl acetate.

As a mixed dispersion method, a proper method may be adopted according to density and viscosity of a solution. Mixed dispersion by use of a mixing equipment such as a disper, Henschel mixer, lodige mixier, kneader, V-shape rotating mixer, roll mill, bead mill, double-shaft kneading machine or spray drying in which a solution and pigments are sprayed in the heated air and the moisture is removed at once is a suitable example of the mixed dispersion method and may be selected. In cases where crushing is performed, conventional crushers such as a hammer mill, ball mill, sand mill and jet mill may be used. It is not limited to a particular crusher since a result of the same quality is obtained with either crusher.

Although the amount of mannosylerythritol lipid attaching to or coating the pigment surfaces is not particularly limited, it is preferably at least 0.1 percent by mass up to 30 percent by mass in order to secure the intended waterproofness and provide excellent fresh skin feeling.

At the time of surface coating treatment in the present invention, simultaneous or multiple surface treatment may be carried out using two or more of conventionally known surface preparation agents. Conventionally known surface treatments include, for example, fluorine compound treatment (perfluoroalkyl phosphate ester treatment, perfluoroalkylsilane treatment, perfluoropolyether treatment, fluorosilicone treatment, fluorinated silicone resin treatment etc.); silicone treatment (methylhydrogen polysiloxane treatment, dimethylpolysiloxane treatment, gas-phase tetramethyltetrahydrogencyclotetrasiloxane treatment etc.); silicone resin treatment (trimethylsiloxysilicate treatment etc.), pendant treatment (a method comprising adding an alkyl chain, etc., after gas-phase silicone treatment); treatment with silane coupling agents; treatment with titanium coupling agents; treatment with aluminum coupling agents; silane treatment (alkylsilane or alkylsilazane treatment etc.); oil solution treatment; polyacrylic acid treatment; metallic soap treatment (stearate or myristate treatment etc.); hydrogenerated lecitin treatment; acrylate resin treatment; metal oxide treatment, or a combination of two or more of these treatments.

In the cosmetics of the present invention, the aforementioned cosmetic pigments can be mixed in a range between 0.1 to 99 percent by mass with respect to mass of a cosmetic. However, more preferable range of the cosmetic pigments is 1 to 80 percent by mass.

It is preferable that the cosmetics of the present invention contains oil solutions that are usually used in cosmetics.

Oil solutions include, for example, avocado oil; linseed oil; almond oil; insects wax; perilla oil; olive oil; cocoa butter; kapok oil; kaya oil; carnauba wax; liver oil; candelilla wax; beef tallow; neat's-foot oil; beef bone fat; hydrogenated tallow; apricot kernel oil; whale wax; hydrogenated oil; wheat germ oil; sesame oil; rice germ oil; rice bran oil; sugar cane wax; sasanqua oil; safflower oil; shea butter; shinagiri oil; cinnamon oil; jojoba wax; shellac wax; turtle oil; soybean oil; tea seed oil; camellia oil; evening primrose oil; corn oil; lard; rapeseed oil; Japanese tung oil; rice bran wax; germ oil; horse fat; parsic oil; palm oil; palm kernel oil; castor oil; hydrogenated castor oil; castor oil fatty acid methyl ester; sunflower oil; grape oil; bayberry wax; jojoba oil; macadamia nut oil; beeswax; mink oil; cottonseed oil; cotton wax; Japan wax; Japan wax kernel oil; montan wax; coconut oil; hydrogenerated coconut oil; coconut oil fatty acid triglyceride; mutton tallow; peanut oil; lanolin; liquid lanolin; reduced lanolin; lanolin alcohol; hard lanolin; lanolin acetate; lanolin fatty acid isopropyl; hexyl laurate; POE lanolin alcohol ether; POE lanolin alcohol acetate; lanolin fatty acid polyethylene glycol; POE hydrogenated lanolin alcohol ether; yolk oil and the like.

Further, in the cosmetics of the present invention, conventionally known surfactants, preservatives, perfumes, moisturizers, salts, solvents, resins, antioxidants, chelate agents, neutralizers, pH adjusters, insect repellents, and bioactive components can be used within the range which would not hinder the object of the present invention.

As pigments, which serve as a base for the cosmetic pigments of the present invention, the same pigments as listed above can be used. It is preferable that such pigments undergo above mentioned surface treatments.

The cosmetics of the present invention are preferably suitable for skin-care products, hair care products, antiperspirant products, makeup products, ultraviolet protection products, perfume solvent and the like. More specifically they include, for example, makeup cosmetics such as foundations, powders, eyeshadow, eye liners, eyebrows, blushers, nail colors, lip balms, lipsticks and mascaras; basic skin care such as emulsions, creams, lotions, sunscreen agents, tanning agents, facial packs, make up removers and face-wash products; hair dyes; hair styling products; body powders; deodorants; depilation agents; soaps; bath agents; hand soaps and perfumes.

Forms of the cosmetics are not particularly limited so that they can take a variety of forms such as liquid, milky liquid, cream, cake, paste, gel, powder, multilayer, mousse or spray.

EMBODIMENTS

Next, embodiments and comparative examples of cosmetic pigments according to the present invention and cosmetics containing such cosmetic pigments will be described.

Manufacturing Embodiment 1

Embodiment of Manufacturing MEL-A, MEL-B and MEL-C

To obtain an inoculum, one loop of colonies of *Pseudozyma antarctica* NBRC 10736 (obtained from: NITE Biological Resource Center) is inoculated in a seed medium (20 ml/500 ml Sakaguchi flask). It is then cultivated overnight at 30 degrees Celsius. The culture medium thus obtained is used as an inoculum. The composition of the seed medium is 4 W/V % Glucose, 0.3 W/V % $NaNO_3$, 0.02 W/V % $MgSO_4 \cdot 7H_2O$, 0.02 W/V % $KH_2PO_4$, and 0.1 W/V % yeast extract. 75 ml of the above inoculum is inoculated in 1.5 L (5-litter Jar) of a production medium and culturing is done under the following condition: 30 degrees Celsius, 300 rpm (stirrer rotation) and 0.5 L/min (Air), using a 5-litter Jar. The composition of the production medium is 3 W/V % soy oil, 0.02 W/V % $MgSO_4 \cdot 7H_2O$, 0.02 W/V % $KH_2PO_4$, and 0.1 W/V % yeast extract. 250 ml of the culture medium is subjected to centrifugation (6500 rpm, 30 min) to remove supernatant and collect a deposition (yeast cells). Added to the deposition is 50 ml of ethyl acetate. After enough stirring, centrifugation (8500 rpm, 30 min) is conducted to obtain supernatant and a deposition. The supernatant is concentrated by an evaporator. It is then eluted with chloroform-acetone (1:0), chloroform-acetone (9:1), chloroform-acetone (1:1), chloroform-acetone (3:7), chloroform-acetone (0:1) by use of silica gel to yield MEL-A, MEL-B and MEL-C fractions. MEL-A, MEL-B and MEL-C contained in the purified fractions respectively has the structure of the above-mentioned general expression (2), general expression (3) and general expression (5).

Although soy oil is used in the above method, MELs can be obtained by the similar method using olive oil.

Manufacturing Embodiment 2

Embodiment of Manufacturing Inverted MEL-B 0.2 ml of a frozen stock of *Pseudozyma tsukubaensis* is inoculated in 20 ml of YM culture medium (1 W/V % glucose, 0.3 W/V % yeast extract, 0.5 W/V % polypeptone, 0.3 W/V % malt extract, pH5.6) in a 500-ml Sakaguchi flask. It is then cultivated overnight at 26 degrees Celsius with 180 rpm to obtain mother inoculum. 0.2 ml of the mother inoculum is again inoculated in 20 ml of YM culture medium in a 500-ml Sakaguchi flask, which is then cultivated overnight at 26 degrees Celsius with 180 rpm to obtain an inoculum. 20 ml of the inoculum is inoculated in 2 L of YM culture medium containing 15 W/V % olive oil in a 5-litter Jar. It is then cultivated for eight days at 26 degrees Celsius with 300 rpm (¼VVM, 0.5 L·air/min). The culture medium is subjected to centrifugation (7900 rpm, 60 min, 4 degrees Celsius) to separate yeast cells (including MEL-B) from supernatant. 80 ml of ethyl acetate is added to each of the yeast fractions, which is then stirred vertically so that the yeast cells are suspended sufficiently. After that, it is subjected to centrifugation (7900 rpm, 30 min, 4 degrees Celsius). Added to the obtained supernatant is saturated brine in equal amount, which is then stirred to obtain an ethyl acetate layer. A proper amount of anhydrous sodium sulphate is added to the ethyl acetate layer and it is left to stand for 30 minutes and evaporated to obtain a crude product of MEL-B. The crude product of MEL-B is eluted with hexane-acetone (5:1), hexane-acetone (1:1) by use of silica gel column to yield a purified MEL-B fraction. MEL-B contained in this purified fraction has the structure of the above-mentioned general expression (4).

Although olive oil is used in the above method, MELs can be obtained by the similar method using soy oil.

Manufacturing Embodiment 3

Embodiment of Manufacturing MEL-C 0.2 ml of a frozen stock of *Pseudozyma hubeiensis* is inoculated in 20 ml of YM culture medium in a 500-ml Sakaguchi flask. It is then cultivated overnight at 26 degrees Celsius with 180 rpm to obtain mother inoculum. 0.2 ml of the mother inoculum is again inoculated in 20 ml of YM culture medium in a 500-ml Sakaguchi flask, which is then cultivated overnight at 26 degrees Celsius with 180 rpm to obtain an inoculum. 20 ml of the inoculum is inoculated in 2 L of YM culture medium in a 5-litter Jar. It is then cultivated for eight days at 26 degrees Celsius with 300 rpm (¼VVM, 0.5 L·air/min). The culture medium is subjected to centrifugation (7900 rpm, 60 min, 4 degrees Celsius) to separate yeast cells (including MEL-C) from supernatant. 80 ml of ethyl acetate is added to each of the yeast fractions, which is then stirred vertically so that the yeast cells are suspended sufficiently. After that, it is subjected to centrifugation (7900 rpm, 30 min, 4 degrees Celsius). Added to the obtained supernatant is saturated brine in equal amount, which is then stirred to obtain an ethyl acetate layer. A proper amount of anhydrous sodium sulphate is added to the ethyl acetate layer and it is left to stand for 30 minutes and evaporated to obtain a crude product of MEL-C. The crude product of MEL-C is eluted with heptane-ethyl acetate (1:1), heptane-ethyl acetate (1:2), heptane-ethyl acetate (1:3) by use of silica gel column to yield a purified MEL-C fraction. MEL-C contained in this purified fraction has the structure of the above-mentioned general expression (5).

Although olive oil is used in the above method, MELs can be obtained by the similar method using soy oil.

Manufacturing Embodiment 5

Embodiment of Manufacturing MEL-D 1 g of MEL-A manufactured in the above Embodiment 1 is suspended in a 50 ml of compound liquid of 0.1 M phosphate buffer (pH 7.0): methanol. After that, 1 g of lipase LPL-311 (Toyobo Co., Ltd.) is added and shaken for 12 hours at 30 degrees Celsius. After reaction, it is extracted and concentrated with ethyl acetate, and a product is isolated with ethyl acetate:methanol (10:1) by use of 20 g of silica gel to obtain 100 mg of a colorless oil product. MEL-D contained in this purified fraction has the structure of the above-mentioned general expression (6).

Manufacturing Embodiment 6

Embodiment of Manufacturing Inverted MEL-D

Using 1 g of inverted MEL-B manufactured in the above Embodiment 2, a reaction is caused in a same fashion as in the Manufacturing Embodiment 5. After that purification is conducted to obtain 95 mg of a colorless oil product. Inverted MEL-D contained in this purified fraction has the structure of the above-mentioned general expression (7).

Manufacturing Embodiment 7

Embodiment of Manufacturing Mannosylerythritol Lipid-Coated Titanium Oxide

After 1000 g of titanium oxide is put in a Henschel mixer, a drop of a solution in which 10.3 g of MEL-A (solid content 98.2 percent by mass of product) is dissolved in 125 g of isopropyl alcohol is mixed so that the titanium oxide is well mixed with it. Thereafter, heating and decompression are applied in the Henschel mixer to remove the ethanol. Pigment powder is taken out from the mixer, crushed and subjected to heat treatment. The titanium oxide is thus obtained whose surface is coated with 1 percent by mass of glucolipids derived from olive oil which comprises fatty acid, mannose and erythritol. By similar processes, sericite, talc, mica, red iron oxide, yellow iron oxide and black iron oxide are each subjected to the surface coating treatment to prepare respective samples.

Surface coating treatments using MEL-B, inverted MEL-B, MEL-C, MEL-D and inverted MEL-D are also conducted in the same way to prepare samples.

Manufacturing Embodiment 8

Embodiment of Manufacturing Mannosylerythritol Lipid-Coated Particulate Titanium Oxide After 1000 g of particulate titanium oxide that is used in ultraviolet light scattering or absorbent is put in a Henschel mixer, a drop of a solution in which 31.5 g of MEL-A (solid content 98.2 percent by mass of product) is dissolved in 125 g of isopropyl alcohol is mixed so that the particulate titanium oxide is well mixed with it. Thereafter, heating and decompression are applied in the Henschel mixer to remove the ethanol. Pigment powder is taken out from the mixer, crushed and subjected to heat treatment. The particulate titanium oxide is thus obtained whose surface is coated with 3 percent by mass of MEL-B derived from olive oil. By similar processes, particulate zinc oxide is subjected to the surface coating treatment to prepare samples.

Surface coating treatments using MEL-B, inverted MEL-B, MEL-C, MEL-D and inverted MEL-D are also conducted in the same way to prepare samples.

Production Comparative Example 1

Samples of titanium oxide, sericite, talc, mica, red iron oxide, yellow iron oxide, black iron oxide, particulate titanium oxide and particulate zinc oxide which are untreated are prepared.

Production Comparative Example 2

Samples of titanium oxide, sericite, talc, mica, red iron oxide, yellow iron oxide, black iron oxide, particulate titanium oxide and particulate zinc oxide which have undergone surface coating treatment with a silicone compound are prepared.

Example 1

Powder Foundation Using MEL-A Surface Coated Pigments

Using the surface coated pigments treated with MEL-A as obtained in the Manufacturing Embodiment 7, a powder foundation having the following compositions is prepared according to the manufacturing method below. Note the unit of measurement used in the list is percent by mass.

| (Ingredients A) | |
| --- | --- |
| Surface-coated sericite | 28.0 |
| Surface-coated talc | 20.0 |
| Surface-coated mica | 16.0 |
| Surface-coated titanium oxide | 8.0 |
| Surface-coated yellow iron oxide | 3.2 |
| Surface-coated red iron oxide | 1.0 |
| Surface-coated black iron oxide | 0.6 |
| Nylon powder | 3.2 |
| (Ingredients B) | |
| Dimethylpolysiloxane (6CS) | 6.0 |
| Dimethylpolysiloxane (10,000CS) | 5.0 |

-continued

| | |
|---|---|
| Purified lanolin | 1.8 |
| Ester oil | 7.2 |
| Total | 100.0 |

(Method for Manufacturing Powder Foundation)

Ingredients A are well mixed using a mixer and ingredients B, which have been evenly dissolved by heating, are gradually added and they are mixed again. After that, they are crushed, sifted through a mesh and stamped out by use of a die to form a product.

Example 2

Powder Foundation Using MEL-B Surface Coated Pigments

Using surface coated pigments treated with MEL-B, a powder foundation is manufactured in the same way as in the Example 1 above.

Example 3

Powder Foundation Using Inverted MEL-B Surface Coated Pigments

Using surface coated pigments treated with inverted MEL-B, a powder foundation is manufactured in the same way as in the Example 1 above.

Example 4

Powder Foundation Using MEL-C Surface Coated Pigments

Using surface coated pigments treated with MEL-C, a powder foundation is manufactured in the same way as in the Example 1 above.

Example 5

Powder Foundation Using MEL-D Surface Coated Pigments

Using surface coated pigments treated with MEL-D, a powder foundation is manufactured in the same way as in the Example 1 above.

Example 6

Powder Foundation Using Inverted MEL-D Surface Coated Pigments

Using surface coated pigments treated with inverted MEL-D, a powder foundation is manufactured in the same way as in the Example 1 above.

Comparative Example 1

Using the untreated pigments prepared in the Production Comparative Example 1, a powder foundation having the same compositions as in the Example 1 is manufactured.

Each powder foundation obtained in the Examples 1 to 6 and the Comparative Example 1 is applied to skin of ten female subjects. Evaluations are made right after application and one hour after application on moist feeling, skin adhesion or impression from use. Table 1 shows the results. A valuation basis for the moist feeling is as follows:

⊚: Sufficient moist feeling is provided.
○: Moist feeling is provided.
Δ: Moist feeling is less provided.
x: No moist feeling is provided.

TABLE 1

| | Treatment type | Moist feeling right after application | Moist feeling one hour after application | Skin adhesion | Impression from use |
|---|---|---|---|---|---|
| Example 1 | MEL-A | ⊚ | ⊚ | Very good | Very good |
| Example 2 | MEL-B | ⊚ | ⊚ | Very good | Very good |
| Example 3 | Inverted MEL-B | ⊚ | ⊚ | Very good | Very good |
| Example 4 | MEL-C | ⊚ | ○ | Good | Very good |
| Example 5 | MEL-D | ○ | ⊚ | Good | Very good |
| Example 6 | Inverted MEL-D | ○ | ⊚ | Good | Very good |
| Comparative Example 1 | Untreated | Δ | X | Bad | Somewhat worse |

As obvious from the table 1, the powder foundations which use surface coated pigments (cosmetic pigments) get evaluations that they have improved moist feeling and its stability, excel in skin adhesion and provide good impression from use.

Example 7

Water-in-Oil Foundation Using MEL-A Surface Coated Pigments

Using surface coated pigments treated with MEL-A obtained in the Manufacturing Embodiments 7 and 8, a water-in oil foundation having the following compositions is prepared according to the manufacturing method below. Note the unit of measurement used in the list is percent by mass.

| | |
|---|---|
| (Ingredients A) | |
| Cyclopenta siloxane | 30.0 |
| Tridecyl isononanoate | 5.0 |
| (Ingredients B) | |
| Surface-coated titanium oxide | 8.5 |
| Surface-coated yellow iron oxide | 1.0 |
| Surface-coated red iron oxide | 0.3 |
| Surface-coated black iron oxide | 0.2 |
| Surface-coated particulate zinc oxide | 5.0 |

-continued

| | |
|---|---|
| Octyltriethoxysilane-treated spherical cellulose powder (Note 1) (Ingredients C) | 3.0 |
| Purified water | remaining amount |
| 1,3 Butylene glycol | 2.0 |
| Preservative | appropriate amount |
| Total | 100.0 |

(Note 1):
OTS-0.5 CELLULOBEADS D-10 (DAITO KASEI KOGYO CO., LTD.)

(Method for Manufacturing Water-in-Oil Foundation)

Ingredients B are evenly mixed and added to Ingredients A. Ingredients C are also evenly mixed and added to the Ingredients A. The mixture is filled in a container and a product is obtained.

Example 8

Water-in-Oil Powder Foundation Using MEL-B Surface Coated Pigments

Using surface coated pigments treated with MEL-B, a water-in-oil powder foundation is manufactured in the same way as in the Example 7 above.

Example 9

Water-in-Oil Powder Foundation Using Inverted MEL-B Surface Coated Pigments

Using surface coated pigments treated with inverted MEL-B, a water-in-oil powder foundation is manufactured in the same way as in the Example 7 above.

Example 10

Water-in-Oil Powder Foundation Using MEL-C Surface Coated Pigments

Using surface coated pigments treated with MEL-C, a water-in-oil powder foundation is manufactured in the same way as in the Example 7 above.

Example 11

Water-in-Oil Powder Foundation Using MEL-D Surface Coated Pigments

Using surface coated pigments treated with MEL-D, a water-in-oil powder foundation is manufactured in the same way as in the Example 7 above.

Example 12

Water-in-Oil Powder Foundation Using Inverted MEL-D Surface Coated Pigments

Using surface coated pigments treated with inverted MEL-D, a water-in-oil powder foundation is manufactured in the same way as in the Example 7 above.

Comparative Example 2

Using the untreated pigments prepared in the Production Comparative Example 1, a water-in-oil foundation having the same compositions as in the Example 7 is manufactured.

Comparative Example 3

Using the siliconized pigments prepared in the Production Comparative Example 2, a water-in-oil foundation having the same compositions as in the Example 7 is manufactured.

(Evaluation Criteria of the Water-in-Oil Foundations)

Ten female subjects participated to use specimens. They evaluated the specimens with respect to moisturizing feeling, skin adhesion and impression from use in a questionnaire format in such a way that 0 point is given if an evaluation is bad, 5 point is given if an evaluation is good. Evaluation result is obtained by taking the average point given by the subjects. Therefore, the higher the point is, the higher evaluation the specimens get. For evaluating temporal stability of the specimens, they are put into ordinary cosmetic containers and stored for three months at 40 degrees Celsius under natural living light. The condition is evaluated visually by the following criteria:

⊚: The condition remains the same.
◯: Some separation occurred.
x: Separation occurred.

The evaluation result is shown in the table 2 below:

TABLE 2

| | Treatment type | Moisturinzing feeling | Skin adhesion | Impression from use | Temporal stability |
|---|---|---|---|---|---|
| Example 7 | MEL-A | 4.8 | 4.8 | 4.5 | ⊚ |
| Example 8 | MEL-B | 5 | 4.8 | 4.9 | ⊚ |
| Example 9 | Inverted MEL-B | 5 | 4.8 | 4.9 | ⊚ |
| Example 10 | MEL-C | 4.8 | 4.6 | 4.6 | ◯ |
| Example 11 | MEL-D | 4 | 4.8 | 4.9 | ⊚ |
| Example 12 | Inverted MEL-D | 4.1 | 4.2 | 4.8 | ⊚ |
| Comparative Example 2 | Untreated | 1.6 | 1.3 | 1 | X |
| Comparative Example 3 | Silicone-treated | 1 | 2 | 0.6 | X |

As obvious from the table 2, the water-in-oil foundations which use surface coated pigments (cosmetic pigments) of the present invention excel in all of the moisturizing feeling, skin adhesion and impression from use. They also excel in the temporal stability. The specimens in the comparative examples separated in two layers because they do not contain a surfactant, and they are inferior in all of the moisturizing feeling, skin adhesion, impression from use and temporal stability. Since the water-in-oil foundations obtained in the examples 7 to 12 excel in skin barrier function and water retention capacity, they provide skins with freshness and moisture. In addition, when applied to skins they showed excellent skin adhesion as well, and temporal stability was also good even if they do not contain any surfactants.

Example 13

Water-in-Oil Sunscreen Using MEL-A Surface Coated Pigments

Using the surface coated pigments treated with MEL-A obtained in the Manufacturing Embodiments 7 and 8, a waterin-oil sunscreen having the following compositions is prepared according to the manufacturing method below. Note the unit of measurement used in the list is percent by mass.

| (Ingredients A) | |
| --- | --- |
| Cyclopenta siloxane | 30.0 |
| Methoxycinnamic acid octyl ester | 3.0 |
| (Ingredients B) | |
| Surface-coated particulate zinc oxide | 10.0 |
| Surface-coated particulate titanium oxide | 5.0 |
| Nylon powder | 1.0 |
| Polymethylmethacrylate powder | 1.0 |
| Silicone resin powder | 1.0 |
| (Ingredients C) | |
| Purified water | remaining amount |
| 1,3 Butylene glycol | 2.0 |
| Preservative | appropriate amount |
| Total | 100.0 |

(Method for Manufacturing Water-in-Oil Sunscreen)

Ingredients B are evenly mixed and added to Ingredients A. Ingredients C are also evenly mixed and added to the Ingredients A. The mixture is filled in a container and a product is obtained.

Example 14

Water-in-Oil Sunscreen Using MEL-B Surface Coated Pigments

Using surface coated pigments treated with MEL-B, a water-in-oil sunscreen is manufactured in the same way as in the Example 13 above.

Example 15

Water-in-Oil Sunscreen Using Inverted MEL-B Surface Coated Pigments

Using surface coated pigments treated with inverted MEL-B, a water-in-oil sunscreen is manufactured in the same way as in the Example 13 above.

Example 16

Water-in-Oil Sunscreen Using MEL-C Surface Coated Pigments

Using surface coated pigments treated with MEL-C, a water-in-oil sunscreen is manufactured in the same way as in the Example 13 above.

Example 17

Water-in-Oil Sunscreen Using MEL-D Surface Coated Pigments

Using surface coated pigments treated with MEL-D, a water-in-oil sunscreen is manufactured in the same way as in the Example 13 above.

Example 18

Water-in-Oil Sunscreen Using Inverted MEL-D Surface Coated Pigments

Using surface coated pigments treated with inverted MEL-D, a water-in-oil sunscreen is manufactured in the same way as in the Example 13 above.

Comparative Example 4

Using the untreated pigments, a water-in-oil sunscreen having the same compositions as in the Example 13 is manufactured.

Comparative Example 5

Using the siliconized pigments, a water-in-oil sunscreen having the same compositions as in the Example 13 is manufactured.

Evaluation on the water-in-oil sunscreens is made in the same way as in the case of the water-in-oil foundations. More specifically, ten female subjects participated to use specimens, and they evaluated the specimens with respect to moisturizing feeling, skin adhesion and impression from use in a questionnaire format in such a way that 0 point is given if an evaluation is bad, 5 point is given if an evaluation is good. Evaluation result is obtained by taking the average point given by the subjects. For evaluating temporal stability of the specimens, they are put into ordinary cosmetic containers and stored for three months at 40 degrees Celsius under natural living light. The condition is evaluated visually by the following criteria:

⊚: The condition remains the same.
○: Some separation occurred.
x: Separation occurred.

The evaluation result is shown in the table 3 below:

TABLE 3

| | Treatment type | Moisturinzing feeling | Skin adhesion | Impression from use | Temporal stability |
| --- | --- | --- | --- | --- | --- |
| Example 13 | MEL-A | 5 | 5 | 4.8 | ⊚ |
| Example 14 | MEL-B | 5 | 5 | 4.8 | ⊚ |
| Example 15 | Inverted MEL-B | 5 | 5 | 4.8 | ⊚ |
| Example 16 | MEL-C | 5 | 5 | 4.8 | ⊚ |
| Example 17 | MEL-D | 5 | 5 | 4.8 | ⊚ |
| Example 18 | Inverted MEL-D | 5 | 5 | 4.8 | ⊚ |
| Comparative Example 4 | Untreated | 1.5 | 1.2 | 1.8 | X |
| Comparative Example 5 | Silicone-treated | 0.9 | 2 | 1 | X |

As obvious from the table 3, the water-in-oil sunscreens which use surface coated pigments (cosmetic pigments) of the present invention excel in all of the moisturizing feeling, skin adhesion and impression from use. They also excel in the temporal stability. The specimens in the comparative examples separated in two layers because they do not contain a surfactant, and they are inferior in all of the moisturizing feeling, skin adhesion, impression from use and temporal stability. Since the water-in-oil sunscreens obtained in the examples 13 to 18 excel in skin barrier function and water retention capacity, they provide skins with freshness and moisture. In addition, when applied to skins they showed excellent skin adhesion as well, and temporal stability was also good even if they do not contain any surfactants.

Example 19

Lip Primer Using MEL-A Surface Coated Pigments

Using the surface coated pigments treated with MEL-A obtained in the Manufacturing Embodiment 8, a lip primer having the following compositions is prepared according to the manufacturing method below. Note the unit of measurement used in the list is percent by mass.

| (Ingredients A) | |
|---|---|
| Ceresin | 4.27 |
| Microcrystalline waxes | 1.55 |
| Deresin candelilla wax | 5.03 |
| High melting paraffin | 3.07 |
| (Ingredients B) | |
| Diisostearyl malate | 1.95 |
| Dipentaerythrite fatty acid ester (1) | 6.22 |
| Adsorption refined lanolin | 2.52 |
| Acetylated lanolin oil | 13.34 |
| Glyceryl tri(2-ethylhexanoate) | 19.02 |
| Liquid paraffin | 7.28 |
| Isotridecyl isononanoate | 3.21 |
| Diglyceryl triisostearate | 4.01 |
| Phenyl-methyl polysiloxane | 2.41 |
| P-hydroxybenzoate ester | 0.07 |
| Diisostearyl malate | remaining amount |
| Natural type vitamine E | 0.05 |
| (Ingredients C) | |
| Surface-coated particulate titanium oxide | 10.0 |
| Total | 100.0 |

Ingredients B are heated to 60 degrees Celsius and mixed well, to which Ingredients C are mixed and dispersed well. Added thereto are Ingredients A, then dissolved in a microwave. After that, they are mixed well by a three roller mill. Again, they are dissolved by heating in a microwave, poured into a mold, then cooled and solidified. By setting the solid in a lipstick container, a product is obtained.

Example 20

Lip Primer Using MEL-B Surface Coated Pigments

Using surface coated pigments treated with MEL-B, a lip primer is manufactured in the same way as in the Example 19 above.

Example 21

Lip Primer Using Inverted MEL-B Surface Coated Pigments

Using surface coated pigments treated with inverted MEL-B, a lip primer is manufactured in the same way as in the Example 19 above.

Example 22

Lip Primer Using MEL-C Surface Coated Pigments

Using surface coated pigments treated with MEL-C, a lip primer is manufactured in the same way as in the Example 19 above.

Example 23

Lip Primer Using MEL-D Surface Coated Pigments

Using surface coated pigments treated with MEL-D, a lip primer is manufactured in the same way as in the Example 19 above.

Example 24

Lip Primer Using Inverted MEL-D Surface Coated Pigments

Using surface coated pigments treated with inverted MEL-D, a lip primer is manufactured in the same way as in the Example 19 above.

Comparative Example 6

Using the untreated pigments prepared in the Production Comparative Example 1, a powder foundation having the same compositions as in the Example 19 is manufactured.

Each lip primer obtained in the Examples 19 to 24 and the Comparative Example 6 is applied to lips of ten female subjects. Evaluations are made, using ⊚, ◯, Δ and x in superiority order, on moisturizing feeling, skin adhesion and impression from use. The evaluation result is shown in the table 4 below:

TABLE 4

| | Treatment type | Moisturizing feeling | Skin adhesion | Impression from use |
|---|---|---|---|---|
| Example 19 | MEL-A | ⊚ | ⊚ | ⊚ |
| Example 20 | MEL-B | ⊚ | ⊚ | ⊚ |
| Example 21 | Inverted MEL-B | ⊚ | ⊚ | ⊚ |
| Example 22 | MEL-C | ⊚ | ⊚ | ⊚ |
| Example 23 | MEL-D | ◯ | ⊚ | ⊚ |
| Example 24 | Inverted MEL-D | ◯ | ⊚ | ⊚ |
| Comparative Example 6 | Untreated | X | X | X |

As obvious from the table 4, the lip primers which use surface coated pigments (cosmetic pigments) of the present invention excel in all of the moisturizing feeling, skin adhesion and impression from use. They also allow lipsticks to spread well and chapped lips are caused less. The lip primer in the comparative example, on the other hand, is inferior in all of the moisturizing feeling, skin adhesion, impression from use and temporal stability.

INDUSTRIAL APPLICABILITY

The cosmetics containing the cosmetic pigments of the present invention have the property that they provide long-lasting moist feeling, (i.e., fresh and enriched feeling). They also excel in skin adhesion and provide good impression from use. For these reasons, they are suitable for use in makeup products such as foundations, eyeshadow and lipsticks or basic skin care such as sunscreen products, emulsions and creams.

The invention claimed is:

1. Cosmetic pigments comprising particles, wherein surfaces of the particles are coated with a mannosylerythritol lipid of formula (1):

[Formula 9]

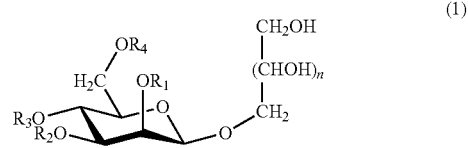

(1)

wherein $R_1$ and $R_2$ are an aliphatic acyl group having 6 to 20 carbons, wherein $R_1$ and $R_2$ are the same as or different from each other, $R_3$ and $R_4$ are a hydrogen or an acetyl group, wherein $R_3$ and $R_4$ are the same as or different from each other, and n is an integer in the range of 2 to 4, wherein the particles, the surfaces of which are coated with the mannosylerythritol lipid, comprise 1 to 3 percent by mass of the mannosylerythritol lipid, wherein the particles, the surfaces of which are coated with the mannosylerythritol lipid, are at least one selected from the group consisting of inorganic powders, organic powders, surfactant metal salt powders, pearl pigments, colored pigments, and metal powder pigments, and wherein the inorganic powders are at least one selected from the group consisting of titanium oxide; zirconium oxide; zinc oxide; cerium oxide; magnesium oxide; barium sulfate; calcium sulfate; magnesium sulfate; calcium carbonate; magnesium carbonate; talc; mica; kaolin; sericite; white mica; synthetic mica; bronze mica; lepidolite; iron mica; lithia mica; silicic acid; silicic anhydride; aluminum silicate; magnesium silicate; magnesium aluminum silicate; calcium silicate; barium silicate; strontium silicate; tungstic acid metal salt; hydroxyapatite; vermiculite; higilite; bentonite; montmorillonite; hectorite; zeolite; ceramics powder; dicalcium phosphate; alumina; aluminum hydroxide; and boron nitride.

2. The cosmetic pigments according to claim 1,
wherein the organic powders are at least one selected from the group consisting of polyamide powder; polyester powder; polyethylene powder; polypropylene powder; polystyrene powder; polyurethane powder; benzoguanamine powder; polymethyl benzoguanamine powder; polytetrafluoroethylene powder; polymethylmethacrylate powder; cellulose; silk powder; nylon powder; nylon 12; nylon 6; acrylic powder; acrylic elastomer; styrene-acrylic acid copolymer; divinylbenzen-styrene copolymer; vinyl resin; urea resin; phenol resin; fluorine resin; silicon resin; acrylic resin; melamine resin; epoxy resin; polycarbonate resin; microcrystal fiber powder; starch powder; and lauroyl lysine.

3. The cosmetic pigments according to claim 1,
wherein the surfactant metal salt powders are at least one selected from the group consisting of zinc stearate; aluminum stearate; calcium stearate; magnesium stearate; zinc myristate; magnesium myristate; zinc cetyl phosphate; calcium cetyl phosphate; and sodium zinc cetyl phosphate.

4. The cosmetic pigments according to claim 1,
wherein colored pigments are at least one selected from the group consisting of inorganic colored pigment; particulate titanium oxide; particulate cerium oxide; particulate zinc oxide; laked tar dye; laked natural dye; and synthetic resin powder comprising a combination thereof.

5. The cosmetic pigments according to claim 1,
wherein the pearl pigments are at least one selected from the group consisting of titanium oxide coated mica; bismuth oxychloride; titanium oxide coated bismuth oxychloride; titanium oxide coated talc; argentine and titanium oxide-coated colored mica.

6. The cosmetic pigments according to claim 1,
wherein the metal powder pigments are at least one selected from the group consisting of aluminum powder, copper powder, and stainless powder.

7. The cosmetic pigments according to claim 1,
wherein the cosmetic pigments are made by dissolving or dispersing the mannosylerythritol lipid in an organic solvent, agitatedly mixing the particles with the mannosylerythritol lipid which is dissolved in the organic solvent, and then removing the organic solvent.

8. The cosmetic pigments according to claim 7,
wherein the organic solvent is selected from the group consisting of ethanol, isopropyl alcohol, isobutyl alcohol, toluene, n-hexane, cyclohexane, acetone, ethyl acetate, and butyl acetate.

* * * * *